United States Patent
Jiao et al.

(10) Patent No.: US 10,406,078 B2
(45) Date of Patent: Sep. 10, 2019

(54) NANO-COMPLEXES FOR ENAMEL REMINERALIZATION

(71) Applicant: Pac-Dent International, Inc., Brea, CA (US)

(72) Inventors: Susan Jiao, Irvine, CA (US); Daniel Wang, Brea, CA (US); Bo Tao, Chino, CA (US); Xiao Yang, La Habra, CA (US)

(*) Notice: Subject to any disclaimer, the term of this patent is extended or adjusted under 35 U.S.C. 154(b) by 0 days.

(21) Appl. No.: 15/816,936

(22) Filed: Nov. 17, 2017

(65) Prior Publication Data

US 2018/0140511 A1    May 24, 2018

Related U.S. Application Data

(60) Provisional application No. 62/424,369, filed on Nov. 18, 2016.

(51) Int. Cl.
    *A61K 6/00*        (2006.01)
    *A61C 19/06*      (2006.01)
    *A61C 7/08*        (2006.01)

(52) U.S. Cl.
    CPC ............ *A61K 6/0017* (2013.01); *A61C 7/08* (2013.01); *A61C 19/063* (2013.01); *A61K 6/0082* (2013.01)

(58) Field of Classification Search
    CPC .................................................. A61K 6/0017
    See application file for complete search history.

(56) References Cited

U.S. PATENT DOCUMENTS 8,889,161 B2 * 11/2014 Latta ................. A61K 8/11
                                                     424/401

* cited by examiner

*Primary Examiner* — Benjamin J Packard

(57) ABSTRACT

The invention relates to nano-sized complexes formed by associating or attaching amorphous calcium phosphate (ACP) and/or amorphous calcium fluoride phosphate (ACFP) with an amphiphilic polymer surfactant (APS) and a bioadhesive polymer. The bioadhesive polymer may serve as a connector or an anchor to attach the nano ACP-APS or ACFP-APS to the tooth surface and to chemically bond the calcium in the enamel to the calcium ions in the nano ACP-APS or ACFP-APS complexes, thus allowing for more controlled release of remineralizing components into the oral cavity. Methods of use of the composition and kits are also disclosed.

21 Claims, No Drawings

NANO-COMPLEXES FOR ENAMEL REMINERALIZATION

CROSS REFERENCE TO RELATED APPLICATIONS

This application claims priority under 35 U.S.C. § 119(e) to U.S. Provisional Application No. 62/424,369, filed Nov. 18, 2016, and entitled "A tooth remineralization composition for tooth remineralization during orthodontic treatment," the disclosure of which is hereby incorporated by reference in its entirety.

BACKGROUND OF THE INVENTION

Field of the Invention

This invention relates to nano-sized complexes formed by associating or attaching amorphous calcium phosphate (ACP) and/or amorphous calcium fluoride phosphate (ACFP) with an amphiphilic polymeric surfactant (APS) as remineralizing agent and a bioadhesive polymer comprising highly charged carboxylated polyanions. In particular, the bioadhesive polymers may serve as a connector or an anchor to attach the nano ACP-APS or ACFP-APS to the tooth surface and to chemically bond the calcium in the enamel to the calcium ions in the nano ACP-APS or ACFP-APS complexes, enabling the ACP and/or ACFP to be sustainably released from the composition over time, including that such a composition may be combined with an orthodontic aligner, for such sustained release and remineralization when said aligner is worn by a subject. The composition may also contain desensitizing agents, antibacterial agents, flavoring agents, enzymes and the like, which additional components may help support dental health. In addition, a method of applying the tooth remineralization composition is provided in the present disclosure.

BACKGROUND INFORMATION

Re-mineralization and demineralization are dynamic processes occurring in the oral environment. The ratio between re-mineralization and demineralization determines the hardness and strength of the tooth structure. White spot lesions and cavities result when the rate of demineralization exceeds the rate of re-mineralization, typically in a process that requires many months or years. Re-mineralization of tooth enamel is the process whereby calcium and phosphate ions are supplied from a source external to the tooth structure to restore mineral ions in demineralized enamel. A range of calcium-phosphate-based re-mineralization systems has been developed for clinical use. One technology is bioactive glass containing calcium sodium phosphosilicate (NOVAMIN™), the second is an un-stabilized amorphous calcium phosphate (ACP, ENAMELON™), and the third involves casein phosphopeptide stabilized amorphous calcium phosphate (CPP-ACP; RECALDENT™).

U.S. Pat. Nos. 5,745,942 and 6,086,374 (each of which is incorporated by reference herein, in its entirety) disclose a novel silica based bioactive glass composition that can be used in conjunction with a delivery agent such as a toothpaste, gel, and the like, having a particle size range <90 μm which will form a rapid and continuous reaction with body fluids due to the immediate and long term ionic release of Ca and P from the core silica particles, to produce a stable crystalline hydroxy carbonate apatite layer deposited onto and into the dentin tubules for the immediate and long term reduction of dentin hypersensitivity and tooth surface re-mineralization. U.S. Pat. No. 8,741,269 (incorporated by reference herein, in its entirety) discloses non-aqueous dentifrice compositions containing a bioacceptable and bioactive glass with improved mouth-feel, foam, and product stability. U.S. Pat. No. 8,715,625 (incorporated by reference herein, in its entirety) discloses a natural anhydrous oral care composition with a limited number of naturally-derived, naturally processed, generally regarded as safe (GRAS) ingredients including an effective amount of a bioactive glass. The topical application of the composition to human teeth cleanses, re-mineralizes and reduces plaque build-up on teeth. A commercial bioactive glass that has been used in the treatment of dental hypersensitivity and enamel re-mineralization is NOVAMIN®, a material which was originally developed as a bone regeneration material.

Amorphous calcium phosphate (ACP) compound is an ideal source of calcium phosphate ions because of its high solubility. The Amorphous Calcium Phosphate (ACP) technology is an un-stabilized calcium and phosphate system that has been developed and commercialized. U.S. Pat. No. 5,427,768 (incorporated by reference herein, in its entirety) discloses calcium phosphate solutions which are supersaturated with respect to calcium phosphate solids and carbon dioxide. The solutions deposit calcium phosphate compounds with or without fluoride on and in the tooth weaknesses such as dental caries, exposed root, or dentin. U.S. Pat. Nos. 5,037,639 and 5,268,167 (each of which is incorporated by reference herein, in its entirety) disclosed the use of amorphous calcium compound such as amorphous calcium phosphate (ACP), amorphous calcium phosphate fluoride (ACFP), and amorphous calcium carbonate phosphate (ACCP) for mineralizing and fluoridating calcified tissues. Amorphous calcium phosphate (ACP) was incorporated into Arm & Hammer's Enamel Care Toothpaste, Discus Dental's Nite White bleaching gel and Premier Dental's Enamel Pro Polishing paste. To keep the calcium ions and phosphate ions from reacting with each other before use, the above products were delivered though a dual-compartment system or delivered in a product with a low water activity.

However, the ACP compounds are unstable when in contact with saliva in the oral environment and transform rapidly into a stable, crystalline form, which has low solubility and thus poor bioavailability. Insoluble calcium phosphates are not easily applied, do not localize effectively at the tooth surface and require acid for solubility to produce ions capable of diffusing into enamel subsurface lesions. On the other hand, soluble calcium and phosphate ions can only be used at very low concentrations due to the intrinsic insolubility of the calcium phosphates, in particular the calcium fluoride phosphates. Soluble calcium and phosphate ions do not substantially incorporate into dental plaque or localize at the tooth surface to produce effective concentration gradients to drive diffusion into the subsurface enamel. The clinical use of calcium and phosphate ions for re-mineralization has not been successful in the past and the efficacy of re-mineralization of the ACP/ACFP remains in doubt because ACP/ACFP transforms to a poorly soluble phase in saliva, and in doing so, may act to promote dental calculus. Several approaches have been developed recently to enhance re-mineralization of ACP/ACFP in tooth enamel.

Casein is the major protein group found in bovine milk and accounts for almost 80% of the total protein. Casein phosphopeptides (CPP) obtained through tryptic digestion have been shown to stabilize amorphous calcium phosphate (ACP) and amorphous calcium fluoride phosphate (ACFP) by binding calcium on the surfaces of the calcium and phosphate ions clusters and hence preventing growth of the calcium and phosphate ion clusters to the critical size for nucleation and phase transformation. The CPP stabilized ACP complex (CPP-ACP) and CPP stabilized ACFP complex (CPP-ACFP) were patented by Reynolds et al. in U.S. Pat. Nos. 6,780,844, 7,312,193, 8,609,071 (each of which is incorporated by reference herein, in its entirety), and the like. Numerous scientific evidences have demonstrated that CPP-CPP and CPP-ACFP can promote the re-mineralization of enamel subsurface lesions and prevent demineralization, as the complexes provide a bioavailable source of calcium and phosphate ions at a high concentration, penetrating into the tooth enamel. In addition, the complexes bind to the surface of dental calculus and prevent or reduce further accretion. These complexes have been incorporated into commercial sugar-free chewing gum (Trident Xtra Care), Recaldent and dental cream (Tooth Mousse and Tooth Mousse Plus, MI Paste and MI Paste Plus). However, the use of CPP-ACP/CPP-ACFP is limited because of milk protein allergy caused by casein.

Jiao et al. (U.S. Pat. No. 9,795,543, herein incorporated by reference in its entirety) have provided nano-sized complexes formed by associating amorphous calcium phosphate (ACP) and/or amorphous calcium fluoride phosphate (ACFP) with an amphiphilic polymeric surfactant (APS). These nano-complexes were free of potential milk protein allergy due to the use of amphiphilic polymeric surfactant as a nano-carrier of ACP. In aqueous solution, the amphiphilic polymeric surfactants (APSs) formed nano-sized assemblies in micellar structure that consisted of a hydrophobic core surrounded by a shell of hydrophilic blocks. The APS micelles served as a nano-dispersant preventing ACP and/or ACFP from aggregating and as a nano-carrier improving the attachment or association of the polymer and ACP and/or ACFP, and thereby, stabilizing ACP and/or ACFP against transforming to a crystalline form.

Methods for preparing the nano-sized complexes and composition comprising the nano-sized complexes are provided in the present invention.

SUMMARY OF THE INVENTION

The present invention relates to nano-sized complexes formed by associating or attaching amorphous calcium phosphate (ACP) and/or amorphous calcium fluoride phosphate (ACFP) with an amphiphilic polymeric surfactant (APS) as remineralizing agent and a bioadhesive polymer comprising highly charged carboxylated polyanions. Methods for preparing the APS stabilized ACP/ACFP nano-sized complexes and compositions thereof are also provided in the present invention. The nano-sized complexes and the compositions may be used in oral care for tooth re-mineralization.

In embodiments, a tooth remineralization composition is disclosed, where the composition is a glutinous paste having nano-complexes containing amorphous phosphate (AP) including amorphous calcium phosphate (ACP), an amorphous calcium fluoride phosphate (ACFP) or a combination thereof, and an amphiphilic polymer surfactant (APS).

In a related aspect, the composition further comprises an bioadhesive polymer. In a further related aspect, the bioadhesive polymer is a highly charged carboxylated polyanion. In another related aspect, the highly charged carboxylated polyanion includes polyacrylic acid sodium salts; polyacrylic acid potassium salts; polyacrylic acid ammonium salts; sodium alginate; carboxymethyl cellulose (CMC); sodium carboxymethyl cellulose (Na-CMC); and combinations thereof.

In one aspect, the bioadhesive polymer bonds the calcium in enamel of teeth to calcium ions in the nano-complexes, thereby effecting sustained release of ACP and/or ACF over a finite period of time.

In another aspect, the composition comprises 0.1% to 10% w/w of said bioadhesive polymers by weight of the total composition weight.

In one aspect, the composition is containing less than 15% of water, more preferably, less than 5% of water by weight of the total composition weight.

In another aspect, the composition comprises desensitizing agents include potassium nitrate, sodium citrate, calcium nitrate, potassium hydroxide, magnesium hydroxide, sodium chloride, calcium phosphate, silver nitrate and sodium citrate and combinations thereof.

In one aspect, the composition further comprises an antibacterial agent.

In another aspect, the composition comprises thickening agents selected from the group consisting of carrageenans, carboxyvinyl polymers, hydroxyethyl cellulose (HEC), natural and synthetic clays, gum karaya, xanthan gum, gum arabic, gum tragacanth, colloidal magnesium aluminium silicate, finely divided silica and combinations thereof.

In one aspect, the composition comprises liquid dispersants selected from glycerin, propylene glycol, polyethylene glycol (PEG) 200, PEG 400, PEG 600, or combinations thereof.

In another aspect, the composition may contain flavoring agents, including citrus flavors, mint, berries, and combinations thereof.

In embodiments, a method of applying a tooth remineralization composition in orthodontic aligner during orthodontic treatment is disclosed including painting with a brush a thin layer of the tooth remineralization composition onto the tooth surface prior to putting on orthodontic aligner; or dispensing directly to the space inside orthodontic aligner prior to wearing the aligner; and rinsing with water to wash away the tooth remineralization composition from the orthodontic aligner after taking off the orthodontic aligner, where the tooth remineralization composition is a glutinous paste comprising nano-complexes containing amorphous phosphate (AP) selected from amorphous calcium phosphate (ACP), an amorphous calcium fluoride phosphate (ACFP) or a combination thereof, and an amphiphilic polymer surfactant (APS).

In a related aspect, the remineralization composition is applied onto the tooth surface inside the orthodontic aligner during orthodontic treatment.

In one aspect, the remineralization composition remains on the tooth surface for a finite period of time, where sustained remineralization is maintained during the orthodontic treatment through the orthodontic aligner.

In another aspect, said method of application is performed each time when the orthodontic aligner is put on or taken off.

In one aspect, the composition further comprises an bioadhesive polymer.

In a related aspect, the bioadhesive polymer is a highly charged carboxylated polyanion.

In embodiments, a kit is disclosed including a tooth remineralization composition, where the composition is a glutinous paste comprising nano-complexes containing amorphous phosphate (AP) including amorphous calcium phosphate (ACP), an amorphous calcium fluoride phosphate (ACFP) or a combination thereof, and an amphiphilic polymer surfactant (APS); a container; a label; and instructions on use of the complex.

In one aspect, the tooth remineralization composition further comprises a highly charged carboxylated polyanion selected including polyacrylic acid sodium salts; polyacrylic acid potassium salts; polyacrylic acid ammonium salts; sodium alginate; carboxymethyl cellulose (CMC); sodium carboxymethyl cellulose (Na-CMC); and combinations thereof.

In a further related aspect, the APS has molecular weight ranging from about 500 to about 500,000 kDa.

DETAILED DESCRIPTION OF THE INVENTION

Before the present composition, methods, and methodologies are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "a nucleic acid" includes one or more nucleic acids, and/or compositions of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Any methods and materials similar or equivalent to those described herein can be used in the practice or testing of the invention, as it will be understood that modifications and variations are encompassed within the spirit and scope of the instant disclosure.

As used herein, "about," "approximately," "substantially" and "significantly" will be understood by a person of ordinary skill in the art and will vary in some extent depending on the context in which they are used. If there are uses of the term which are not clear to persons of ordinary skill in the art given the context in which it is used, "about" and "approximately" will mean plus or minus <10% of particular term and "substantially" and "significantly" will mean plus or minus >10% of the particular term. In embodiments, composition may "contain", "comprise" or "consist essentially of" a particular component of group of components, where the skilled artisan would understand the latter to mean the scope of the claim is limited to the specified materials or steps "and those that do not materially affect the basic and novel characteristic(s)" of the claimed invention.

As used herein, "glutinous" means like glue in texture; sticky. For example, glutinous paste may contain negatively charged polymers, abrasive silica, nanosized silica or combinations thereof.

The nano-sized complexes of the present invention are composed of amorphous calcium phosphate (ACP) and/or amorphous calcium fluoride phosphate (ACFP) associated or complexed with amphiphilic polymer surfactant (APS) and a bioadhesive polymer. By association or complexation with the amphiphilic polymer surfactant, ACP and/or ACFP can be stabilized against the conversion to crystalline apatite, where the bioadhesive can associate the ACP and/or ACFP with tooth surfaces, and thus enamel re-mineralization of ACP and/or ACFP may be enhanced.

"Amphiphilic polymers" refer to molecules that both attract and repel water. The amphiphilic polymer surfactants (APS) are composed of hydrophilic (water-loving) and hydrophobic (water-hating) parts. As amphiphilic polymers reduce surface tension and are used as surfactants, "amphiphilic polymer" and "amphiphilic polymer surfactant" are interchangeably used in the present invention.

By association or attaching ACP and/or ACFP molecules with the amphiphilic polymer, which serves as a nano-carrier, ACP and/or ACFP are further stabilized against the conversion to crystalline apatite, and thus enamel re-mineralization can be enhanced. Based on the above-mentioned mechanism, a desirable requirement on the dispersant is the ability to stabilize ACP and/or ACFP against aggregation to large particles and transforming to the crystalline form. Further, the bioadhesive polymers may serve as a connector or an anchor to attach the nano ACP-APS or ACFP-APS to the tooth surface and to chemically bond the calcium in the enamel to the calcium ions in the nano ACP-APS or ACFP-APS complexes, enabling the ACP and/or ACFP to be sustainably released from the composition over time, including that such a composition may be combined with, for example, an orthodontic aligner, for such sustained release and remineralization when said aligner is worn by a subject.

Other instruments that may be used with the composition, for example, but not limited to, include tooth brushes, tongue scrapers, dental floss, dental picks, mouth guards, and orthodontic corrective devices, e.g., braces and retainers. Instruments for use in the oral cavity are not limited to cleaning and orthodontic corrective devices. Other instruments include objects designed to be used in the oral cavity, such as pacifiers (also known as a comforter, or soother), and chew toys for toddlers and infants, such as teething rings.

Such instruments may be combined with the compositions as disclosed. As the surface(s) of the instrument is exposed in the oral cavity, the composition on the surface of the instrument is released into the oral cavity.

Incorporating the composition directly onto the instrument may also be accomplished by use of a porous material. The instrument may be manufactured from the porous material, or coated with the same. Generally, the material contains pores which the composition resides in. The composition is released when the instrument is used, e.g., in the oral cavity. If the pores release the composition contained there, the porous material may be treated by exposure to the composition to refill the pores. Thus, the composition may be released from, or captured in the pores.

Amphiphilic polymers meet the above-mentioned requirement. Moreover, the amphiphilic polymer surfactant (APS) can prevent ACP and/or ACFP from aggregation to large particles and stabilize ACP and/or ACFP against transforming to the stable crystalline form and improve the attachment or association of ACP and/or ACFP molecules with the polymer (APS).

In another aspect, the APSs are selected from the group of non-ionic polymer surfactants and ionic polymer surfactants and the mixture thereof. The non-ionic polymer surfactants include (but not limited to) di-block polyethylene oxide and polypropylene oxide (PEO-PPO) copolymer (with PPO as hydrophobic blocks and PEO as hydrophilic blocks); di-block polyethylene oxide and poly (butylene oxide) (PEO-PBO) copolymer (with PBO as hydrophobic blocks and PEO as hydrophilic blocks); tri-block PEO-PPO-PEO copolymer; tri-block PEO-PBO-PEO copolymer and the like. The ionic polymer surfactants include (but not limited to)

polyalkylene co acrylic acid; polyalkylene co maleic anhydride; polyalkylene co polyacrylic acid; polyalkylene co maleic acid; polyalkylene sulfonic acid co maleic acid; and polystyrene co acrylic acid; polystyrene co maleic anhydride; polystyrene co polyacrylic acid; polystyrene co maleic acid; polystyrene sulfonic acid co maleic acid. The ionic surfactants may also be polycationic polymers, such as polyalkylene polyamine; polystyrene polyamine, the copolymers consisting of cationic polyamine, chitosan and its derivatives, and the like.

In another aspect, the APS have molecular weight ranging from 500 to 500,000 kDa.

As stated above, the composition as disclosed contains a bioadhesive, and more specifically, a bioadhesive polymer comprising highly charged carboxylated polyanions. In embodiments, the highly charged carboxylated polyanion includes polyacrylic acid sodium salts; polyacrylic acid potassium salts; polyacrylic acid ammonium salts; sodium alginate; carboxymethyl cellulose (CMC); sodium carboxymethyl cellulose (Na-CMC); and combinations thereof.

However, the composition may also comprise antimicrobial agents (i.e. bactericides) in any suitable form. The antimicrobial agents may be present in an amount up to the maximum levels permitted by appropriate regulatory authorities. For example, any one or combination of the following antimicrobial agents may be used: triclosan; cetyl pyridinium chloride (CPC); domiphen bromide; quaternary ammonium salts; sanguinarine; suitable fluorides; alexidine; octonidine; and EDTA.

Flavourings may also be included. Suitable flavourings may exhibit fragrant properties. Suitable flavourings may be added during the manufacturing process in the form of flavoured oils. The flavourings may form amounts of about 0-30 wt. % or about 0-10 wt. % of film.

The flavourings may be chosen from natural oils, synthetic flavour oils, flavouring aromatics, oleo resins and extracts derived from plants, leaves, flowers, fruits and so forth, and combinations thereof.

Flavour oils which may be used include any one or combination of the following: spearmint oil; cinnamon oil; peppermint oil; clove oil; bay oil; thyme oil; cedar leaf oil; oil of nutmeg; oil of sage; and oil of bitter almonds.

Also useful are artificial, natural or synthetic fruit flavours such as vanilla, chocolate, coffee, cocoa and citrus oil, including lemon, orange, grape, lime and grapefruit and fruit essences including apple, pear, peach, strawberry, raspberry, cherry, plum, pineapple, apricot and so forth. These flavourings can be used individually or in a mixture. Commonly used flavours include mints, such as peppermint, artificial vanilla, cinnamon derivatives, and various fruit flavours, whether employed individually or in admixture. Flavourings such as aldehydes and esters including cinnamyl acetate, cinnamaldehyde, citral, diethylacetal, dihydrocarvyl acetate, eugenyl formate, and p-methylanisole, and so forth may also be used.

As required, the compositions as disclosed herein may comprise a sweetening agent or a combination of sweetening agents. The sweetening agents may be present in an amount of less than about 30 wt. %, but more typically less than about 20 wt. %.

Typical sweeteners include monosaccharides, disaccharides and polysaccharides such as any one or combination of the following: xylose; ribose; glucose (dextrose); mannose; galactose; fructose (i.e. levulose); sucrose (i.e. sugar); and maltose; an invert sugar (i.e. a mixture of fructose and glucose derived from sucrose); partially hydrolysed starch; corn syrup solids; dihydrochalcones; monellin; steviosides; and glycyrrhizin.

Additionally, water-soluble artificial sweeteners such as soluble saccharin salts may be used. For example, any one or combination of the following artificial sweeteners may be used: sodium or calcium saccharin salts; cyclamate salts; sodium, ammonium or calcium salts of 3,4-dihydro-6-methyl-1,2,3-oxathiazine-4-one-2,2-dioxide; potassium salts of 3,4-dihydro-6-methyl-1,2,3-oxathiazine-4-one-2,2-dioxide (acesulfame-K); sucralose; and the free acid form of saccharin.

Moreover, dipeptide based sweeteners such as any one or combination of the following may be used: L-aspartic acid derived sweeteners, such as L-aspartyl-L-phenylalanine methyl ester (aspartame); L-alpha-aspartyl-N-(2,2,4,4-tetramethyl-3-thietanyl)-D-alaninamide hydrate; methyl esters of L-aspartyl-L-phenylglycerin and L-aspartyl-L-2,5-dihydrophenyl-glycine; L-aspartyl-2,5-dihydro-L-phenyl-alanine; and L-aspartyl-L-(1-cyclohexyen)-alanine.

Water-soluble sweeteners derived from naturally occurring water-soluble sweeteners, such as a chlorinated derivative of ordinary sugar (i.e., sucrose) may also be used.

In embodiments, the composition may contain enzymes. The enzyme may be of animal source, microbial source (e.g. *Clostridium histolyticum*) as well as of plant source (papaya-papain). In embodiments, the proteolytic enzyme is an endogenous enzyme. In some other embodiments, the proteolytic enzyme is an exogenous enzyme.

The enzyme may be naturally occurring, semi synthetic or synthetic enzyme. The naturally occurring, synthetic or semi-synthetic enzymes can be obtained by commonly known laboratory procedures. In some embodiments, the enzyme can be provided by cellular structures, e.g., isolation from bacterial culture.

In examples, the enzyme is a cysteine protease (also known as thiol proteases) with catalytic mechanism that involves a nucleophilic cysteine thiol. An example of a cysteine protease is papain.

In examples, the proteolytic enzyme is a metalloprotease, specifically, a zinc protease.

In examples, the proteolytic enzyme is specific and/or selective to collagen.

Optionally, the composition may contain a saliva stimulating agent, useful for example in amelioration of dry mouth may be included. Any orally acceptable saliva stimulating agent can be used, including without limitation food acids such as citric, lactic, malic, succinic, ascorbic, adipic, fumaric, and tartaric acids, and mixtures thereof. One or more saliva stimulating agents are optionally present in a saliva stimulating effective total amount.

In embodiments, at least one antiplaque (e.g., plaque disrupting) agent may be included. Any orally acceptable antiplaque agent may be used, including without limitation stannous, copper, magnesium and strontium salts, dimethicone copolyols such as cetyl dimethicone copolyol, papain, glucoamylase, glucose oxidase, urea, calcium lactate, calcium glycerophosphate, strontium polyacrylates and mixtures thereof.

In embodiments, at least one optional desensitizing agent, including potassium citrate, potassium chloride, potassium tartrate, potassium bicarbonate, potassium oxalate, potassium nitrate, strontium salts, and mixtures thereof, are included.

The following examples will further describe the present invention without, however, at the same time, constituting any limitation thereof.

EXAMPLES

Example 1. Remineralization Paste Composition 1

| Composition Ranges of the Ingredients in Remineralization Paste 1 | |
|---|---|
| Glycerin | 20-35 |
| Sodium Polyacrylic acid | 0.2-2 |
| Xylitol | 3-5 |
| Sodium Tripolyphosphate | 0.3-1.0 |
| Potassium Nitrate | 3-5 |
| APS-ACPF | 2-10 |
| Silica | 10-20 |
| Methyl Salicylate | 0.2-0.5 |
| Flavors | 0.2-0.8 |

Water content in the paste was less than 2%. Viscosity was measured with Brookfield Rheometer. The viscosity was between 20,000 centipoises to 40,000 centipoises (cps).

Example 2. Remineralization Paste Composition 2

| Composition Ranges of the Ingredients in Remineralization Paste 2 | |
|---|---|
| Glycerin | 20-40 |
| Coconut oil | 1-5 |
| Xylitol | 3-5 |
| Ammonium Acryloyldimethyltaurate/VP Copolymer | 0.5-3 |
| Cetyl Esters | 1-5 |
| Potassium Nitrate | 3-5 |
| APS-ACPF | 2-10 |
| Silica | 10-20 |
| Sodium Tripolyphosphate | 0.3-1.0 |
| Methyl Salicylate | 0.2-0.5 |
| Flavors | 0.2-0.8 |

Water content in the paste was less than 2%. Viscosity was measured with Brookfield Rheometer. The viscosity was between 5,000 centipoises to 20,000 centipoises (cps).

It is understandable that the above compositions or formulations are only examples of the type of formulations. The invention disclosed and defined extends to all alternative combinations of two or more of the individual features mentioned or evident from the text or drawings. All of the combinations constitute various alternative aspects of the invention.

We claim herein:

1. A tooth remineralization composition, wherein the composition is a glutinous paste comprising nano-complexes containing amorphous phosphate (AP) selected from amorphous calcium phosphate (ACP), an amorphous calcium fluoride phosphate (ACFP) or a combination thereof, and an amphiphilic polymer surfactant (APS).

2. The tooth remineralization composition according to claim 1, wherein the composition further comprises a bioadhesive polymer.

3. The tooth remineralization composition according to claim 2, wherein the bioadhesive polymer is a highly charged carboxylated polyanion.

4. The tooth remineralization composition according to claim 3, wherein the highly charged carboxylated polyanion is selected from the group consisting of polyacrylic acid sodium salts; polyacrylic acid potassium salts; polyacrylic acid ammonium salts; sodium alginate; carboxymethyl cellulose (CMC); sodium carboxymethyl cellulose (Na-CMC); and combinations thereof.

5. The tooth remineralization composition according to claim 4, wherein the bioadhesive polymer bonds the calcium in enamel of teeth to calcium ions in the nano-complexes, thereby effecting sustained release of ACP and/or ACF over a finite period of time.

6. The tooth remineralization composition according to claim 2, wherein said composition comprises 0.1% to 10% w/w of said bioadhesive polymers by weight of the total composition weight.

7. The tooth remineralization composition according to claim 1, wherein the composition is containing less than 15% of water by weight of the total composition weight.

8. The tooth remineralization composition according to claim 1, wherein the composition comprises desensitizing agents selected from the group consisting of potassium nitrate, sodium citrate, calcium nitrate, potassium hydroxide, magnesium hydroxide, sodium chloride, calcium phosphate, silver nitrate and sodium citrate and combinations thereof.

9. The tooth remineralization composition according to claim 1, wherein the composition further comprises an antibacterial agent.

10. The tooth remineralization composition according to claim 1, wherein the composition comprises thickening agents selected from the group consisting of carrageenans, carboxyvinyl polymers, hydroxyethyl cellulose (HEC), natural and synthetic clays, gum karaya, xanthan gum, gum arabic, gum tragacanth, colloidal magnesium aluminium silicate, finely divided silica and combinations thereof.

11. The tooth remineralization composition according to claim 1, wherein the composition comprises liquid dispersants selected from glycerin, propylene glycol, polyethylene glycol (PEG) 200, PEG 400, PEG 600, or combinations thereof.

12. The tooth remineralization composition according to claim 1, wherein the composition may contain flavoring agents, selected from the group consisting of citrus flavors, mint, berries, and combinations thereof.

13. A method of applying a tooth remineralization composition in orthodontic aligner during orthodontic treatment comprising:
   painting with a brush a thin layer of the tooth remineralization composition onto the tooth surface prior to putting on orthodontic aligner; or
   dispensing directly to the space inside orthodontic aligner prior to wearing the aligner; and
   rinsing with water to wash away the tooth remineralization composition from the orthodontic aligner after taking off the orthodontic aligner,
   wherein the tooth remineralization composition is a glutinous paste comprising nano-complexes containing amorphous phosphate (AP) selected from amorphous calcium phosphate (ACP), an amorphous calcium fluoride phosphate (ACFP) or a combination thereof, and an amphiphilic polymer surfactant (APS).

14. The method of claim 13, wherein the remineralization composition is applied onto the tooth surface inside the orthodontic aligner during orthodontic treatment.

15. The method of claim 13, wherein the remineralization composition remains on the tooth surface for a finite period of time, whereby sustained remineralization is maintained during the orthodontic treatment through the orthodontic aligner.

16. The method of claim 13, wherein the said method of application is performed each time when the orthodontic aligner is put on or taken off.

17. The method of claim 13, wherein the composition further comprises an bioadhesive polymer.

18. The method of claim 17, wherein the bioadhesive polymer is a highly charged carboxylated polyanion.

19. A kit comprising:
 a tooth remineralization composition, wherein the composition is a glutinous paste comprising nano-complexes containing amorphous phosphate (AP) selected from amorphous calcium phosphate (ACP), an amorphous calcium fluoride phosphate (ACFP) or a combination thereof, and an amphiphilic polymer surfactant (APS);
 a container;
 a label; and
 instructions on use of the complex.

20. The kit of claim 19, wherein the tooth remineralization composition further comprises a highly charged carboxylated polyanion selected from the group consisting of polyacrylic acid sodium salts; polyacrylic acid potassium salts; polyacrylic acid ammonium salts; sodium alginate; carboxymethyl cellulose (CMC); sodium carboxymethyl cellulose (Na-CMC); and combinations thereof.

21. The tooth remineralization composition according to claim 1, wherein the composition is containing less than 5% of water by weight of the total composition weight.

* * * * *